US006136538A

United States Patent [19]
Olivo et al.

[11] Patent Number: 6,136,538
[45] Date of Patent: Oct. 24, 2000

[54] SILENT INDUCIBLE VIRUS REPLICONS AND USES THEREOF

[75] Inventors: Paul D. Olivo; Sondra Schlesinger, both of St. Louis, Mo.

[73] Assignee: Washington University, St. Louis, Mo.

[21] Appl. No.: 09/227,556

[22] Filed: Jan. 8, 1999

[51] Int. Cl.[7] .............................. C12Q 1/68; C12Q 1/70; C07H 21/04; A61K 48/00
[52] U.S. Cl. ..................................... 435/6; 536/24; 536/1; 435/5; 435/69.1; 435/91.4; 435/456; 435/457; 435/375; 435/320.1; 424/199.1; 424/218.11; 424/93.2
[58] Field of Search ................................. 435/41, 69.1, 5, 435/6, 325, 366, 7.1, 7.2, 7.21, 320.1, 91.4, 456, 457, 375; 424/93.1, 93.21, 93.2, 199.1, 218.11; 536/24.1

[56] References Cited

U.S. PATENT DOCUMENTS

| | | | |
|---|---|---|---|
| 5,418,132 | 5/1995 | Olivo | 435/5 |
| 5,591,579 | 1/1997 | Olivo et al. | 435/6 |
| 5,789,245 | 8/1998 | Dubensky, Jr. et al. | 435/320.1 |

OTHER PUBLICATIONS

Stabell, E. and Olivio, pp. Isolation of a cell line . . . , *J. Virological Methods* 38, pp. 195–204, 1992.
Berglund et al., Semliki Forest Virus Expression System: Production of Conditionally Infectious Recombinant Particles, *Bio/Technology* 11:916–920 (1993).
Berglund et al, Enhancing immune responses using suicidal DNA vaccines, *Nature Biotechnol.* 16:562–565 (1998).
Bredenbeek et al., Animal RNA virus expression systems, *Semin. Virol.* 3:297–310 (1992).
Dubensky et al., Sindbis Virus DNA–Bases Expression Vectors: Utility for In Vitro and In Vivo Gene Transfer, *J. Virol.* 70:508–519 (1996).
Frolov et al., Alphavirus–based expression vectors: Strategies and applications, *Proc. Natl. Acad. Sci. USA* 93:11371–11377 (1996).
Hariharan et al., DNA Immunization against Herpes Simplex Virus: Enhanced Efficacy Using a Sindbis Virus–Based Vector, *J. Virol.* 72:950–958 (1998).
Herweijer et al., A Plasmid–Based Self–Amplifyng Sindbis Virus Vector, *Human Gene Therapy* 6:1161–1167 (1995).
Olivo et al, A Cell Line That Expresses a Reporter Gene in Response to Infection by Sindbis Virus: A Prototype for Detection of Positive Strand RNA Viruses, *Virol.* 198:381–384 (1994).
Schlesinger, RNA Viruses as Vectors for the Expression of Heterologous Proteins, *Mol. Biotechnol.* 3:155–165 (1995).
Polo et al., DNA Vaccines with a kick, *Nature Biotechnol.* 16:517–518 (1998).

*Primary Examiner*—David Guzo
*Assistant Examiner*—Jon Schuman
*Attorney, Agent, or Firm*—Howell & HaferKamp, LC

[57] ABSTRACT

A recombinant cell stably transformed with a cDNA of a silent, inducible replicon encoding a recombinant protein is disclosed. Transcription of the replicon cDNA is under the control of a silent promoter inducible by a DNA virus and expression of the recombinant protein is dependent upon the presence of the DNA virus in the cell. The cell can be engineered to package the replicon upon infection by the DNA virus, leading to intercellular amplification of expression of the recombinant protein. Where the recombinant protein is a reporter gene product, the recombinant cell may be used in an assay for detecting DNA viruses. A kit for performing such an assay is also provided.

23 Claims, 9 Drawing Sheets

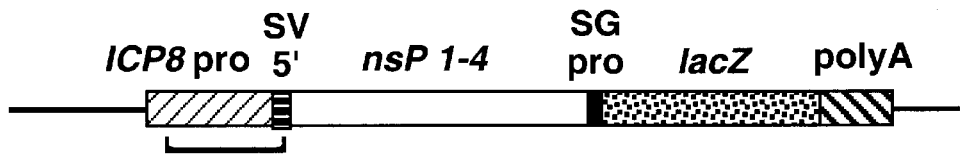

Fig. 1A

```
         -330
          |
5'- TCCGGaCGGCGAGCTGCTGCGCGGCGCCCCGGCCGGCGGCCCGGTTTATT

CGCGTCGGCCCGGCCGGCCGGGCTTATGGACCGCCGGCGGCCGACAGGAG
         -230
          |
    AGTGACGTAGCCGGTGGGCGTGGCCGCTATTATAAAAAAAGTGAGAACGC

GAAGCGTTCGCACTTTGTCCTAATAATATATATATTATTAGGACAAAGTG
         -130
          |
    CGAACCGTTCGCGTTCTCACTTTTTTTTATAATAGCGGCCACGCCCACCGG

CTGATGACGCGCGGGGCGTGGGAGGGGCTGGGGCGGTCCGGCACGCCCCC
         -30
          |
    AGGTAAAGTGTACATATACCAACCGCATACCtcgagATTGACGGCGTAGT

ACACACTATTGAATCAAACAGCCGACCAATTGCACTACCATCACAATG.//.-3'
```

Fig. 1B

SILENT INDUCIBLE VIRUS REPLICONS AND USES THEREOF

REFERENCE TO GOVERNMENT SUPPORT

This invention was made with U.S. Government support under Grant No. AI11377 awarded by the National Institutes of Health. The U.S. Government has certain rights in the invention.

BACKGROUND OF THE INVENTION (1) Field of the Invention

This invention generally relates to the field of virology and, more particularly, to inducible viral replicons and to their use as expression vectors for making recombinant proteins and for detecting other viruses.

(2) Background of the Invention

Replicon RNAs are self-replicating RNA molecules that contain the genetic information needed for virus replication but frequently lack one or more of the genes encoding the structural proteins needed for virus assembly. There have been numerous reports of using replicons derived from alphaviruses such as Sindbis virus and Semliki Forest virus (SFV) as vectors for gene expression. See e.g., Bredenbeek et al., *Semin. Virol.* 3:297–310; 1992; Berglund et al., *Bio/Technology* 11:916–920, 1993; and Schlesinger, S., *Mol. Biotechnol.* 3:155–165, 1995. Alphaviruses are particularly suited for such use because these positive-strand RNA viruses have a broad host range, replicate exclusively in the cytoplasm of infected host cells, and their genomic RNA alone is sufficient to initiate replication and productive infection (Polo et al., *Nature Biotechnol.* 16:517–518, 1998). The original studies involved preparing a cDNA of an RNA replicon encoding a heterologous protein instead of the structural proteins, in which transcription of the cDNA was under the control of the bacteriophage SP6 promoter, transcribing the cDNA in vitro and transfecting the RNA transcripts into susceptible cultured cells (Xiong et al., Science 243:1188–1191, 1989).

More recently, several reports have described transcribing replicon cDNAs from promoters recognized by RNA polymerase II after transfection of the cDNA into cells (Dubensky et al., *J. Virol.* 70:508–519, 1996; Hariharan et al., *J. Virol.* 72:950–958, 1998; Herweijer et al., *Human Gene Therapy* 6:1161–1167, 1995; Berglund et la., *Nature Biotechnol* 16:562–565, 1998; and Polo et al., supra). However, because these constructs are constitutively expressed in the host cells, this approach could not be used to stably transform cells with a replicon cDNA derived from a cytopathic alphavirus which rapidly shuts down host protein synthesis and kills the host cell. Stable transformation of cells has been accomplished using a replication-defective Sindbis virus cDNA (Olivo et al., Virol. 198:381–384, 1994; U.S. Pat. No. 5,591,579). However, this strategy requires infection with Sindbis virus or transfection with Sindbis replicon RNA to obtain expression of the heterologous protein encoded by the Sindbis virus defective genome.

U.S. Pat. No. 5,789,245 to Dubensky et al., states that a stably transformed host cell line can be achieved by placing a replicon cDNA under the control of a transcriptionally inactive, but inducible, promoter. The only examples of such inducible replicon cDNAs that were specifically described in this reference are replicon cDNAs containing viral or cellular promoters stated to be active only in terminally differentiated cells. The reference states that such constructs can be used to transform undifferentiated cells with induction of the replicon requiring addition of a cell differentiation agent such as retinoic acid. However, the only such construct actually made contained the U3 region of the long terminal repeat (LTR) from Moloney murine leukemia virus (Mo-MLV) and when this luciferase-encoding replicon cDNA was transfected into undifferentiated F9 cells, luciferase expression above background (i.e., mock infected cells) was detected (FIG. 14), suggesting that at least some basal transcription from the Mo-MLV LTR occurred.

Most inducible systems can tolerate a certain amount of basal transcription either because it is several orders of magnitude lower than induced levels or because the level of basal transcription does not result in detectable levels of the gene product. If, however, the transcribed product is a replicon derived from a cytopathic RNA virus, a single molecule of functional replicon RNA that finds its way to the cytoplasm will initiate an autocatalytic cycle of RNA replication and transcription which will result in the inhibition of host protein synthesis and cell death. Thus, generation of stable cell lines containing an inducible promoter operably linked to a replicon cDNA derived from a cytopathic RNA virus requires that the promoter be completely silent in the absence of induction. However, in addition to the apparent basal transcription of the replicon in the '245 patent, this reference did not describe any experiments or show any data to establish that stably transformed cells could actually be achieved with the Mo-MLV-replicon cDNA or with constructs containing any of the listed inducible promoters. This reference also did not disclose or suggest using a silent promoter inducible by a DNA virus to launch an RNA replicon from a transfected cDNA and, furthermore, did not disclose or suggest packaging the launched RNA replicon to produce RNA virus particles that infect surrounding cells and thereby achieve intercellular amplification of the amount of heterologous protein synthesized whose expression was originally induced by the DNA-virus. Moreover, the '245 patent did not teach or suggest the use of any of its constructs for the detection of DNA viruses.

U.S. Pat. No. 5,418,132 to Olivo disclosed a method for detecting an infectious herpes virus which employs a cell line stably transformed with a chimeric gene having a reporter gene under the control of a promoter from the herpes virus that is induced by transactivating substances produced by the infecting herpes virus. The reference states that promoters from beta, or early herpes virus genes are preferred because of their ability to be transactivated. However, this reference did not disclose or suggest using beta-gene promoters from herpes virus to induce transcription of a replicon cDNA encoding a heterologous protein upon response to herpes virus infection nor did it teach using a second virus to achieve intercellular amplification of the signal induced by the herpes virus. Moreover, the skilled artisan could not have predicted from the data presented in the '132 patent whether beta-gene promoters from herpes virus would have the requisite degree of regulatory stringency when operably linked to a replicon cDNA to allow stable transformation of cells with replicon cDNAs derived from a cytopathic RNA virus.

It would be desirable therefore, to provide a means for launching a replicon RNA in a cell stably transformed with a cDNA of the replicon where the replicon is not transcribed in a cell in the absence of an inducing agent. It would also be desirable if such a stably transformed cell could be used for detecting the presence of infectious DNA viruses with the sensitivity and specificity necessary for a diagnostic assay.

SUMMARY OF THE INVENTION

Briefly, therefore, the present invention is directed to novel compositions and methods which permit inducible expression of recombinant proteins. In one embodiment, the invention provides a stably transformed, recombinant cell which only expresses a recombinant protein in the presence of a DNA virus. The recombinant protein is encoded by a cDNA of a self-replicating vector (replicon) derived from a positive-strand RNA virus. The cDNA is operably linked to a silent promoter inducible by the DNA virus and, upon infection of the recombinant cell by the DNA virus, the cDNA is transcribed into a replicon RNA which is transported to the cytoplasm where it is translated to produce viral replication enzymes which generate multiple copies of the replicon. This autoamplification results in enhanced expression of the recombinant protein. In preferred embodiments, the recombinant cell also expresses a defective helper virus which encodes the proteins needed for packaging the replicon into infectious RNA virus particles that can infect surrounding cells to achieve intercellular amplification of the amount of recombinant protein expressed. If the silent inducible promoter is from the infecting DNA virus and the recombinant protein is a reporter gene product, the cell can be used to detect the presence of the DNA virus in a sample. In preferred embodiments, the silent inducible promoter is a beta-gene promoter from a herpes virus, which allows the stably transformed cell to be used to detect the herpes virus.

In another embodiment, the invention provides a method for detecting a DNA virus in a sample. The method involves contacting the sample with a stably transformed, recombinant cell which comprises a silent promoter from the DNA virus operably linked to a cDNA comprising a replicon of a positive-strand RNA virus. The replicon encodes a reporter gene product which is expressed only if the DNA virus is present in the cell to induce transcription of the cDNA. Thus, detection of the reporter gene product indicates the sample contains infectious particles of the DNA virus. In some embodiments, the method includes quantifying the number of infectious particles of the DNA virus that are in the sample.

In other embodiments, the stably transformed cell is used to screen compounds for anti-viral activity against the inducing virus and for measuring antibody responses of individuals infected with or vaccinated against the inducing DNA virus.

In yet another embodiment, the invention provides a kit for detecting a DNA virus in a sample which comprises a supply of recombinant cells packaged in a container. The recombinant cells are stably transformed with a polynucleotide comprising a silent promoter from the DNA virus operably linked to a cDNA of a replicon of a positive-strand RNA virus, wherein the replicon comprises a nucleotide sequence encoding a reporter gene product and wherein transcription of the cDNA is dependent upon the presence of the DNA virus. In a preferred embodiment, the kit also includes a set of reagents for detecting expression of the reporter gene product.

The invention also provides a method for producing a recombinant protein. The method comprises the steps of (a) providing a recombinant cell stably transformed with a polynucleotide comprising a silent promoter inducible by a DNA virus operably linked to a cDNA of a replicon of a positive-strand RNA virus, wherein the replicon comprises a nucleotide sequence encoding the recombinant protein and wherein transcription of the cDNA is dependent upon the presence of the DNA virus; (b) incubating the recombinant cell with the DNA virus; and (c) isolating the recombinant protein.

Among the several advantages of the present invention may be noted the provision of a stably transformed, recombinant cell which expresses a reporter gene product only upon infection by a DNA virus; the provision of a rapid and sensitive assay for specifically detecting the DNA virus; the provision of such an assay that provides intercellular amplification of a reporter gene signal induced by the DNA virus; and the provision of a kit for detecting the DNA virus.

BRIEF DESCRIPTION OF THE DRAWINGS

FIGS. 1A and 1B illustrate a promoter-replicon cDNA construct (pICP8SINrep/lacZ) used to prepare a preferred embodiment of the invention, showing in FIG. 1A a schematic diagram (not drawn to scale) of a chimeric polynucleotide comprising the HSV-1 ICP8 promoter (pro) operably inked to a cDNA of a Sindbis virus replicon (SV) which contains a region encoding nonstructural proteins (nsP) and the lacZ gene under the control of the Sindbis subgenomic promoter (SG), with the bracket indicating the region surrounding the junction of the ICP8 promoter and the 5' terminus of the Sindbis replicon genome whose sequence is shown in FIG. 1B (SEQ ID NO:1), where the arrow indicates the predicted start of transcription based on mapping studies of the ICP8 transcript, upper-case nonbold letters indicate HSV-1 sequences, bold letters indicate Sindbis virus sequences, lower-case letters indicate bases introduced during cloning to create restriction sites BspM II and Xho I (underlined).

(FIG. 3A) a bar graph of β-galactosidase activity in three Vero cell lines transformed with pICP8SINrep/lacZ that were transfected with the defective helper cDNA plasmid (p987DHBBNeo) and then mock infected or infected with HSV-1 in the presence of acyclovir; (FIG. 3B) a bar graph of β-galactosidase activity in baby hamster kidney (BHK) cells inoculated with media from the HSV-1 infected Vero cell cultures of FIG. 3A; and (FIG. 3C) a bar graph of β-galactosidase activity in BHK cells inoculated with media from cultures of pICP8SINrep/lacZ -transformed Vero cell lines that were first infected with HSV-1 and then transfected with the helper plasmid or mock-transfected.

FIG. 4B shows a bar graph of β-galactosidase activity in BHK cells inoculated with media from the HSV-1 infected Vero cell cultures of FIG. 4A at 15 and 24 h post infection.

DESCRIPTION OF PREFERRED EMBODIMENTS

Figure 2:
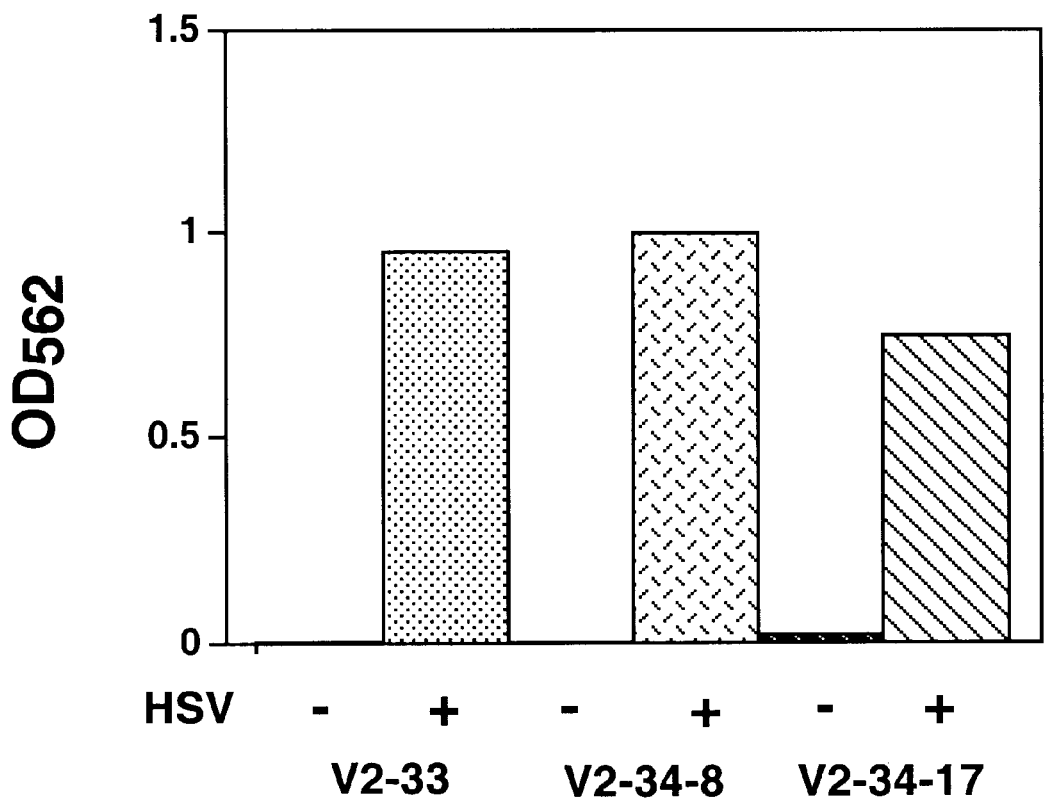
FIG. 2 illustrates HSV-1-induced expression of β-galactosidase in Vero cells transformed with pICP8SINrep/lacZ showing a bar graph of β-galactosidase activity expressed by three transformed cell lines that were mock-infected (−) or infected (+) with wild-type HSV-1 in the presence of acyclovir.

In accordance with the present invention, a stably transformed cell containing a silent, inducible virus replicon is provided. The invention is based on the inventors' discovery that replicon cDNAs under the control of certain DNA virus-inducible promoters, particularly herpes virus beta-gene promoters, are transcriptionally inactive in the absence of the inducing DNA virus.

In the context of this disclosure, the following terms shall be defined as follows unless otherwise indicated:

"inducing DNA virus" means a composition minimally comprising one or more transactivating proteins or biologically active fragments thereof of a DNA virus that can induce a silent promoter operably linked to a replicon, with the term including naturally occurring infectious DNA virus particles as well as mutant viruses;

"infectious" when used to describe a DNA virus means that virus particles are capable of entering cells and initiating a virus replication cycle, whether or not this leads to production of new DNA virus particles;

"positive-strand RNA virus" means a virus whose genome consists of one or more positive-sense RNA molecule(s) and which replicates its genome through a negative-sense RNA intermediate;

"silent, inducible promoter" means a promoter inducible by a DNA virus that is completely silent in the absence of the DNA virus as well as in the absence of any other agent that may induce the promoter;

"recombinant cell" means a cell stably transformed or transiently transfected with a polynucleotide encoding a recombinant protein;

"recombinant protein" means any biologically active or inactive protein, polypeptide, or fragment thereof that is synthesized in a recombinant cell by expression of a nucleotide sequence present on a polynucleotide introduced into the cell;

"replicon" means a replication-competent recombinant RNA molecule derived from a positive-strand RNA virus that contains the genetic information needed for virus replication and includes constructs lacking one or more of the structural proteins needed for packaging as well as packaging-competent constructs, i.e., encode all the structural proteins;

"transfected cell" means a cell containing an exogenously introduced nucleic acid molecule; and "stably transformed cell" or "transformed cell" means a cell containing an exogenously introduced nucleic acid molecule which is present in the nucleus of the cell and may be stably integrated into the chromosomal DNA of the cell.

A stably transformed cell according to the present invention is a vertebrate cell that is susceptible to infection by the inducing DNA virus. A cell is susceptible to infection if the infecting virus can enter the cell and proceed far enough in its replication cycle to express proteins necessary to trans-activate the inducible promoter. It will be understood by those skilled in the art that cell lines susceptible to infection by a particular DNA virus can be readily identified by searching the literature for known susceptible cell lines and/or by screening candidate cell lines using well-known procedures requiring only routine experimentation. Susceptible cells for DNA viruses include, but are not limited to baby hamster kidney cells, Vero (African green monkey) cells, rabbit skin fibroblasts, 3T3 mouse cells, mink lung cells and the like.

The cell is stably transformed with a polynucleotide comprising a cDNA of a replicon derived from a positive-strand RNA virus. The replicon, which can be packaging-defective or packaging-competent, can be derived from any of a number of positive-strand RNA viruses, including viruses from the following families: Togaviridae, Coronaviridae, Astroviridae, Flaviviridae, Picornaviridae and Nodaviridae. Examples of replicons from these viral genera have been described (see, e.g., Schlesinger, S., *Mol. Biotechnol.* 3:155–165, 1995; Bredenbeek, et al., Semin. Virol 3:297–310, 1992) or can be readily prepared by the skilled artisan.

The replicon comprises a nucleotide sequence encoding at least one recombinant protein. This nucleotide sequence may be inserted anywhere in the replicon as long as it does not interfere with transcription or translation of the replicon. If a packaging-defective replicon is desired, the nucleotide sequence can be inserted in place of one or more of the genes encoding the structural proteins. For example, in replicons derived from an alphavirus such as Sindbis or from another virus in which the structural proteins are encoded by a subgenomic mRNA transcribed from a subgenomic promoter, the nucleotide sequence can be introduced immediately downstream of and under the regulatory control of the subgenomic RNA promoter in place of the structural protein-encoding sequences.

Where the transformed cell is to be used to detect a DNA virus, the recombinant protein is a reporter gene product. Any reporter gene product that is detectable is suitable for use in the present invention. The reporter gene product is preferably one that can easily be assayed for or detected in a cell. One enzyme that has proved to be particularly useful as a reporter gene product is β-galactosidase. Preferably, a bacterial β-galactosidase is used, and most preferably the β-galactosidase from *E. Coli* that is encoded by the LacZ gene. Other reporter gene products useful in this invention generally include hydrolases or oxidoreductases and, in particular, such enzymes as β-glucosidase, β-glucuronidase, β-hexosaminidase, luciferase, phospholipase, phosphatase, etc. Green fluorescent protein (GFP) is another reporter gene product useful in the invention.

A nucleotide sequence encoding β-galactosidase or luciferase is particularly preferred for use in this invention because of the numerous methods known to detect expression of these enzymes and the relative sensitivity of such methods. Among these methods include histochemical assays involving a chromogenic or fluorogenic substrate which permits detection of β-galactosidase activity by a change in the color of the cell that can be detected macroscopically or microscopically. The use of luciferase provides an enzymatic assay that is more sensitive than the calorimetric or fluorometric β-galactosidase assay. Expression of luciferase may be detected by known luminometric methods using luciferin as the enzyme substrate.

The replicon cDNA which encodes the recombinant gene is operably linked to a promoter inducible by a DNA virus. The inducible promoter can be any promoter inducible by a DNA virus that is transcriptionally inactive in the absence of the DNA virus or other inducing agents to which the cell would normally be exposed. For example, it is known in the art that infection of mammalian cells by DNA viruses induces expression of a number of silent cellular genes such as interferon and other cytokines whose products are involved in the immune response to viral infection. It is contemplated that the skilled artisan can readily test any particular promoter for use in the invention by linking the promoter to a replicon cDNA that encodes a very sensitive reporter gene product such as luciferase, transfect cells with the construct and assay for the reporter gene product in the absence of any inducing agents. Those constructs from which reporter gene product is not detectably expressed above background levels, i.e., in mock-transfected cells, are then used to stably transform cells and the transformed cells are assayed for production of reporter gene product that is undetectable in the absence of a DNA virus but that is induced upon infection of the transformed cell with DNA virus.

Preferably, the virus-inducible promoter is from a gene of a DNA virus whose expression is specifically induced by one or more transactivating proteins of the DNA virus. Such constructs are useful to detect the presence of the DNA virus in a sample, i.e, infectious particles of the virus that enter the cell and synthesize the viral transactivating protein(s) that induce transcription of the replicon cDNA.

A particularly preferred inducible promoter for use in the invention is a herpes virus beta-gene promoter, which are tightly regulated. All herpes viruses have a linear double-stranded DNA genome and they all replicate in the nucleus of infected cells where viral gene expression during viral replication occurs as an ordered cascade. Genes expressed during viral replication are organized on the genome in a very straightforward manner; there are few overlapping genes, very few spliced genes, and the regulatory elements (for example, promoters) are immediately upstream of the open reading frames. All known herpes viruses have three major classes of herpes virus genes, α, β, and γ, which have the same basic temporal pattern of expression during viral replication.

Alpha genes, also called immediate-early genes, are expressed very early after infection and the expression of each alpha gene does not require any other viral gene or gene product. The products of the alpha genes are predominantly involved in regulation of viral gene expression.

Beta (early) genes are expressed only after the alpha genes because their expression depends on the presence of one or more of the alpha gene products which act as transcriptional activators to upregulate the expression of the beta genes. Thus, one way that beta genes have been defined is by the observation that their expression from the viral genome is not reduced in infected cells when viral DNA synthesis is blocked, but there is a virtual absence of expression of their RNA transcripts when production of alpha gene products is prevented by blocking protein synthesis. The products of beta genes are primarily enzymes involved in viral nucleic acid synthesis and metabolism.

Gamma (late) genes are expressed either primarily (γ1) or exclusively (γ2) following viral DNA synthesis. Gamma gene products are primarily structural components of the virion.

Many studies have analyzed the regulation of herpes virus gene expression using isolated herpes virus genes or isolated herpes virus promoters, outside the context of the viral genome. This experimental approach has contributed to the identification of the cis- and trans-acting factors involved in the regulation of the expression of many herpes virus genes. It is generally recognized that the beta-gene promoter is both necessary and sufficient for the transactivation of beta genes by alpha gene products.

The eight known human herpes viruses are herpes simplex virus type 1 (HSV-1), herpes simplex virus type 2 (HSV-2), human cytomegalovirus (HCMV), varicella-zoster virus (VZV), Epstein-Barr virus (EBV), human herpes virus 6 (HHV6), human herpes virus 7 (HHV7), and human herpes virus 8 (HHV8) and the complete genomic sequence of each of these viruses is known other than HHV8, for which a partial sequence is known (HSV-1, McGeoch et al., *Nucleic Acids Res* 14:1727–1745, 1986, McGeoch et al., *J Gen Virol* 69:1531–1574, 1988, GenBank Accession Nos.: X14112, D00317, D00374, and S40593); HSV-2, McGeoch et al., *J. Gen. Virol.* 72, 3057–3075, 1991, *GenBank Accession No.:* Z86099; HCMV, Chee et al., DNA Seq 2:1–12, 1991, *GenBank Accession No.:* X17403; EBV, Baer et al., *Nature* 310:207–211, 1984, *GenBank Accession Nos.:* V01555, J02070, K01729, K01730, V01554, X00498, X00499, and X00784; VSV, Davidson and Scott, *J Gen Virol* 67:1759–1816, 1986, *GenBank Accession Nos.:* X04370, M14891, and M16612; HHV6, Gompels et al., *Virology* 209:29–51, 1995, *GenBank Accession No.*: X83413; HHV7, Nicholas, *GenBank Accession No.*: U43400; and HHV8, Russo et al., *Proc. Natl. Acad. Sci. U.S.A.* 93:14862–14867, 1996, *GenBank Accession No.:* U75698). Analysis of this sequence data has shown that the beta genes represent a limited number of genes in the genomes of all herpes viruses which have been studied and that beta genes are highly conserved in the herpes virus family.

For example, in HSV-1 there are fourteen genes that have been classified as beta genes: UL2, UL5, UL8, UL9, UL12, UL23, UL29, UL30, UL39, UL40, UL42, UL50, UL52, and UL53 (Roizman et al., Herpes Simplex Viruses and Their Replication, Raven Press, Ltd. N.Y., pp. 1795–1841, 1990). These genes encode respectively, a uracil DNA glycosidase, a DNA helicase, a component of the DNA helicase/primase complex, an origin of DNA replication binding protein, a DNA exonuclease, a nucleoside kinase, a single-stranded DNA binding protein, a DNA polymerase, a ribonucleotide reductase large subunit, a ribonucleotide reductase small subunit, a double-stranded DNA binding protein which acts as a polymerase processivity factor, a dUTPase, a primase, and a protein kinase. All but one of these enzymes, the protein kinase, has been shown to be involved in DNA metabolism or to be directly involved in synthesis of viral DNA.

Based on standard DNA and predicted protein sequence alignment paradigms, it has been determined that the other herpes viruses have homologues for most or all of the fourteen HSV-1 beta genes (Davison et al., *J. Gen. Virol.* 67:1759–1816 1986; Baer et al., *Nature* 310:207–211, 1984; Chee et al., *Curr. Top. Microhiol. immunol.* 154: 125–169, 1990). A listing of the homologous beta genes in the human herpes virus family is shown in Table 1 below.

base pairs of the coding region. The restriction enzyme(s) suitable for digesting the herpes virus genomic DNA may be chosen by analysis of the reported sequence for that genome. The cloning strategy is designed so that transcription from the beta promoter begins at the 5' end of the replicon. If transcription is initiated too far upstream or downstream of the 5' terminus of the replicon it will not be recognized by its own RNA replicase and will not undergo self-amplification.

In some embodiments of the invention, the stably transformed cell has been engineered to be able to package the replicon transcribed from the cDNA after infection with the inducing DNA virus. This ability to package the replicon allows intercellular amplification of the amount of recom-

TABLE 1

Beta Genes of Human Herpes Viruses

| HSV-1 | HSV-2 | VZV | EBV | HCMV | HHV6 | HHV7 | HHV8 |
| --- | --- | --- | --- | --- | --- | --- | --- |
| UL2 | UL2 | gene 59 | BKRF3 | UL114 | U81 | U81 | ORF 46 |
| UL5 | UL5 | gene 55 | BBLF4 | UL105 | U77 | U77 | ORF 44 |
| UL8 | UL8 | gene 52 | BBLF3 | UL102 | U74 | U74 | ORF 41 |
| UL9 | UL9 | gene 51 | (nh) | (nh) | U73 | U73 | (nh) |
| UL12 | UL12 | gene 48 | BGLF5 | UL98 | U70 | U70 | ORF 37 |
| UL23 | UL23 | gene 36 | BXLF1 | (nh) | (nh) | (nh) | ORF 21 |
| UL29 | UL29 | gene 29 | BALF2 | UL57 | U41 | U41 | ORF 6 |
| UL30 | UL30 | gene 28 | BALF5 | UL54 | U38 | U38 | ORF 9 |
| UL39 | UL39 | gene 19 | BORF2 | UL45 | U28 | U28 | ORF 61 |
| UL40 | UL40 | gene 18 | BaRF1 | (nh) | (nh) | (nh) | ORF 60 |
| UL42 | UL42 | gene 16 | BMRF1 | UL44 | U27 | U27 | ORF 59 |
| UL50 | UL50 | gene 8 | BLLF2 | UL72 | U45 | U45 | ORF 54 |
| UL52 | UL52 | gene 6 | BSLF1 | UL70 | U43 | U43 | ORF 56 |
| US3 | US3 | gene 66 | (nh) | (nh) | (nh) | (nh) | not determined |
| (nh) | (nh) | (nh) | (nh) | UL101 | (nh) | (nh) | (nh) |
| (nh) | (nh) | (nh) | (nh) | UL84 | U55 | U55 A/B | (nh) |
| (nh) | (nh) | (nh) | (nh) | UL112 | U79 | U79 | (nh) |

(nh): no homologue

In those cases which have been studied, the products of these conserved genes have displayed remarkable conservation of function and all, except for the protein kinase gene, have been shown to have a role in viral DNA synthesis or metabolism. Moreover, in all cases studied, these genes exhibit a pattern of expression consistent with their being classified as beta genes.

As described below, the inventors herein have demonstrated that promoters from two different beta-genes, the HSV-1 UL29 gene and the HCMV UL45 gene, possess the necessary degree of regulatory stringency such that no detectable transcription of the replicon cDNA occurs until infection of the cell with the corresponding herpes virus. Thus, it is believed that at least a majority of herpes virus beta-gene promoters will be operable in the present invention.

Beta-gene promoter sequences can be isolated using sequence information and techniques known in the art. For example, one method for isolating the promoter for any particular beta-gene from a desired herpes virus is by PCR amplification of genomic template obtained from cells infected with the desired herpes virus. The PCR primers are designed from the reported sequence for that promoter to amplify an approximately 600 bp fragment extending from approximately −500 bp to approximately +100 bp relative to the site of transcription initiation. Another method for isolating the promoters for these beta genes is by cloning into a vector a restriction fragment of the genome of the desired herpes virus which contains about 500 base pairs of DNA upstream of the coding region of the gene and about 100 binant protein expressed. When the inducing virus infects a cell that is able to package the induced replicon, virus particles containing the replicon will infect surrounding cells in a cell culture monolayer. Thus, a single cell infected with a DNA virus will lead to many cells expressing the recombinant protein. If the recombinant protein is a reporter gene, this extra layer of signal amplification provides an even more sensitive assay for detecting infectious DNA viruses.

The ability to package the replicon can be accomplished by using packaging-competent replicons such as double subgenomic Sindbis replicons (Frolov et al., *Proc. Natl. Acad. Sci.* USA 93:11371–11377, 1996). Alternatively, the cell can be transfected with or stably transformed with a cDNA of a defective helper RNA. As used herein, "defective helper RNA" means a replication-defective recombinant RNA molecule derived from the same positive-strand RNA virus as the replicon and is designed to contain the structural protein genes as well as the cis-acting sequences required for replication. The helper cDNA is operably linked to a promoter that either allows constitutive expression of helper RNA, such as the rous sarcoma virus (RSV) long terminal repeat sequence (LTR), or preferably, is linked to an inducible promoter. In a particularly preferred embodiment, the helper cDNA is operably linked to a silent promoter that is specifically induced by the same DNA virus that induces transcription of the replicon cDNA. For example, the replicon cDNA and the helper cDNAs could each be linked to the same or different beta-gene promoter from HCMV, i.e., both could be linked to the UL45 promoter or one cDNA could be transcribed from the UL45 promoter while the other cDNA is transcribed from the UL57 promoter. The two cDNAs can be introduced into the cell as part of a single polynucleotide or can be comprised on separate polynucleotides. Replicase/transcriptase functions supplied by translation of the replicon RNA in the virus-infected cell lead not only to its own replication but also act in trans to allow replication and transcription of the helper RNA which results in synthesis of structural proteins that can package the replicon.

In accordance with one embodiment of the invention, the above-described stably transformed cells can be used in a method for producing a recombinant protein. The method is performed by adding an inducing DNA virus to cells stably transformed with a promoter activated by the inducing DNA virus operably linked to a replicon cDNA encoding the recombinant protein. The cells are cultured in suitable standard culture medium for a time period sufficient for replication of both the inducing virus and the replicon to occur and then the recombinant protein is isolated from the cells. Alternatively, if the replicon is engineered to express a secreted protein, then the recombinant protein can be isolated from the culture medium. In this example, the inducing DNA virus may carry out an abortive infection. It is only necessary for the infected cells to synthesize the products of the alpha genes to activate the beta promoters.

Transformed cells according to the invention can also be used in a method for detecting a DNA virus in a sample. The sample may be any material from a person, animal or the environment which can be placed into a fluid or fluid environment and includes biological fluids such as blood, semen, nasopharyngeal swabs, cerebrospinal fluids and the like. The method is performed by contacting the sample with cells stably transformed with a promoter inducible by the DNA virus operably linked to a replicon cDNA encoding a reporter gene product. Typically, a portion of the sample is added to a culture of the cells in a suitable standard culture medium and then the cells are cultured for a time period sufficient for the infectious cycle of the DNA virus to proceed and for replication of the transcribed replicon to occur. The culture is then examined for presence of the reporter gene product which may be assayed in the culture medium, in extracts of the cells or directly in the cells, i.e., by histochemical staining, depending on the type of reporter gene product.

The invention also provides a kit for detecting a DNA virus. The kit is prepared by placing in a container a supply of the above-described genetically-engineered cells sufficient to conduct an assay or a number of assays in accordance with the invention. Preferably, the kit is also provided with one or more reagents necessary for detecting the reporter gene product, placed in separate container(s). An instruction manual may also be included in the kit.

The method and cells of this invention are useful for the detection of DNA viruses and in particular herpesviruses.

The following examples of the present invention are offered by way of illustration and are not to be considered in a limiting sense.

EXAMPLE 1

This example illustrates the preparation of a recombinant polynucleotide containing the HSV-1 ICP8 promoter operably linked to a Sindbis replicon.

The HSV-1 ICP8 gene, also known as the UL29 gene, is a beta gene encoding infected-cell protein 8 (ICP8), which is the HSV-1 major single-strand DNA-binding protein (McGeoch, D. J., et al., *J. Gen. Virol.* 69:1531–1574, 1988; Quinn, J. P., et al., Nuc. Acids. Res. 13:8143–8163, 1985). Expression of ICP8 is dependent on the regulatory proteins encoded by HSV-1 immediate-early genes such as ICP0 and ICP4 (O'Hare, P., et al., *J Virol.* 53:751–60, 1985; Quinlan, M. P., et al., *Mol. Cell Biol.* 5:957–96330, 1985; Su, L., et al., *J of Virol.* 61:615–620, 1987). The 5' of the ICP8 transcript has been mapped (Su, L., et al., *J of Virol.* 61:615–620, 1987), which made it very straightforward to design a DNA construct in which the cDNA of a Sindbis virus replicon would be linked to the HSV-1 ICP8 promoter in such a way that transcription from this chimeric gene would yield an RNA transcript with a 5' end compatible with a functional replicon.

The ICP8 promoter sequence was amplified from purified HSV-1 genomic DNA by PCR by using synthetic oligonucleotides (DNAgency, Inc.) flanking this region. The primers used were 30 and 35-mer oligonucleotides (upstream primer: 5'-GTT TGT CTG GCG GAT CCG GAC GGC GAG CTG-3' (SEQ ID NO:2); downstream primer: 5'-CCA TGG CTC GAG GTA TGC GGT TGG TAT ATG TAC AC-3' (SEQ ID NO:3). The 5' and 3' termini contained BspE I and Xho I sites respectively, to facilitate cloning. The amplification was done in 20 cycles using KlenTaq-LA enzyme (Wayne Barnes, Washington University, St. Louis, Mo.) in the presence of 2.2 M betaine using the following conditions: 30 s at 94° C., 30 s at 60° C., 1 min at 68° C. The PCR product was digested with BspE I and Xho I and the product was then cloned into NgoM I and Aho I digested plasmid pICP6/987SINrep/LacZ to produce pICP8SINrep/LacZ. The former plasmid had been generated from p987SINrep/LacZ by placing a Xho I site at the 5' terminus of the cDNA of SINrep/LacZ. Plasmid and promoter identity were confirmed by restriction and nucleotide sequence analysis. All plasmid DNAs used herein for transfections were purified on CsCl gradients.

EXAMPLE 2

This example illustrates the activity of pICP8SINrep/LacZ in uninfected cells and HSV-1-infected cells.

To determine if the pICP8SINrep/LacZ construct was silent in uninfected cells and inducible by HSV-1, the plasmid 2 μg was transiently transfected into BHK-21 and Vero cells obtained from American Tissue Type Collection (ATCC, Manassas, Va.). For this and the experiments described below, BHK cells were grown in alpha-minimum essential medium (MEM) supplemented with 10% fetal bovine serum (FBS), nonessential amino acids, 100 U/ml penicillin and 100 mg/ml streptomycin (pen/strep), while Vero cells were propagated in Dulbecco's MEM (DMEM) containing 10% FBS and pen/strep. Twenty-four hours after transfection with pICP8SINrep/LacZ, the cells were infected with HSV-1 (KOS strain), which was obtained from Mark Challberg (NIH, Bethesda, Md.) and grown and titered on Vero cells. Eighteen hours after HSV-1 infection, β-galactosidase activity of extracts from the transfected BHK and Vero cells was measured by a colorimetric assay using the substrate chlorophenolred-b-D-galactopyranoside, (CPRG, Boehringer Mannheim, Indianapolis, Ind.) at a final concentration of 5 mM in a 0.2 M potassium phosphate buffer, pH 7.8, with 1 mM MgCl2. Extracts were made in this buffer containing 1% Triton X-100 and 1 mM dithiothreitol. A sample of the extract (10–50 μl) was mixed with 50 μl of substrate in a microtiter plate well. After incubation for 1 to 2 h at room temperature, the optical density at a wavelength of 562 nM ($OD_{562}$) was measured with a THERMOmax microplate reader using SOFTmax software (Molecular Devices, Sunnyvale, Calif.). The assay was shown to be linear up to an $OD_{562}$ of 3.0.

In the transfected BHK cells, β-galactosidase was detected in the absence of HSV-1 infection, although the levels increased after infection. In contrast, the transfected Vero cells showed β-galactosidase activity only after infection with HSV-1 (data not shown).

EXAMPLE 3

This example illustrates that Vero cells transfected with both pICP8SINrep/LacZ and a defective helper cDNA produces infectious SINrep/LacZ particles.

The results described in Example 2 did not necessarily indicate that HSV-1 was able to induce SINrep/Lacz in the Vero cells because mere induction of β-galactosidase activity does not establish that the replicon genome is intact and that translation of β-galactosidase is dependent on prior replication and transcription of the replicon. For example, HSV-1 can nonspecifically transactivate a foreign gene even when the latter is placed several kb downstream of a pol II promoter (Olivo, P. D., et al., *Virology* 198:381–384, 1994). Thus, a second and essential criterion for establishing induction of a replicon by a DNA virus is that infectious, extracellular particles are produced when induction occurs in the presence of a defective helper RNA that provides the structural proteins for packaging.

To determine if a functional SINrep/LacZ replicon was being transcribed in Vero cells, the cells were cotransfected with pICP8SINrep/LacZ and a defective helper plasmid, p987DHBBneo, which was made from pDHBB, a defective helper cDNA which has the Sindbis virus structural protein genes downstream of the subgenomic RNA promoter (Bredenbeek, P. J., et al., *J Virol.* 67:6439–6446, 1993). p987DHBBneo was constructed by positioning the cDNA of DHBB immediately 3' of the Rous sarcoma virus promoter and inserting an IRES element-neo gene cassette downstream of the stop codon for the structural proteins in the 3' nontranslated region of the DHBB genome (Frolov, I., and S. Schlesinger. unpublished results).

Figure 3A:
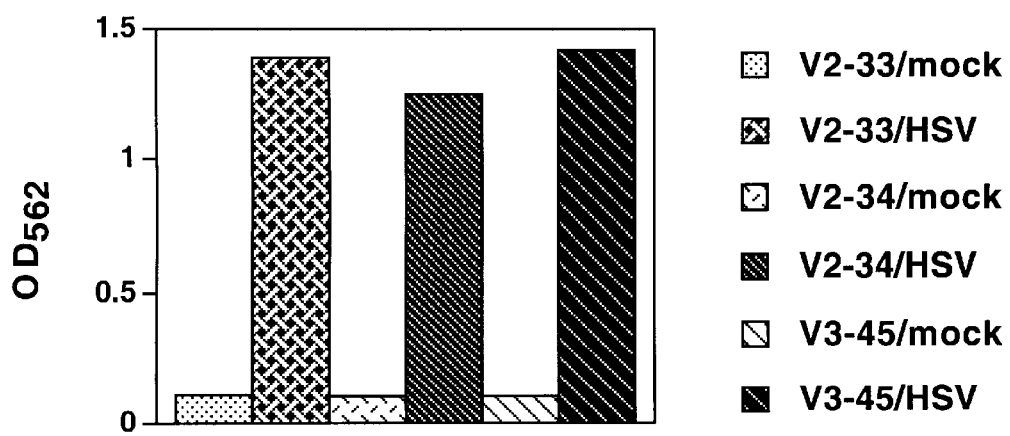
FIGS. 3A–C illustrate complementation of the HSV-1-induced SINrep/lacZ replicon by a defective packaging helper virus expressing the Sindbis structural proteins showing.

Separate groups of Vero cells were treated as follows: co-transfected with pICP8SINrep/LacZ and p987DHBBNeo and infected with HSV-1; transfected with only pICP8SINrep/LacZ and infected with HSV-1; mock-infected; co-transfected with p987DHBBNeo and a control plasmid, pICP8LacZ, which contains the lacZ gene directly downstream of the ICP8 promoter. The protocol was further modified by the addition of acyclovir to block HSV-1 DNA synthesis and HSV-1 production. The absence of HSV-1 in the supernatant fluids of the transfected Vero cells made it possible to detect packaged Sindbis virus replicons in these samples without cytopathic effects attributable to HSV-1 progeny. Naive BHK cells were inoculated with samples of media taken from the variously treated Vero cells and then assayed for β-galactosidase activity by a histochemical staining assay. In brief, cell monolayers were washed one time with one ml of phosphate buffered saline (PBS, pH 7.2), then fixed in 2% formaldehyde, 0.4% glutaraldehyde in PBS for 5 m. After washing twice with PBS, cells were incubated at room temperature in staining solution (5-bromo-4-chloro-3 indolyl-galactopyranoside (X-gal, Sigma, St. Louis, Mo.) 1 mg/ml, 4 mM potassium ferricyanide, 4 mM potassium ferrocyanide, and 2mM MgCl$_2$ in PBS. β-galactosidase-positive BHK cells were detected only when inoculated with media obtained from Vero cells that had been co-transfected with pICP8SINrep/LacZ and p987DHBBNeo and infected with HSV-1. (These data are not shown, but see FIG. 3 for similar results with stable cell lines.)

EXAMPLE 4

This example illustrates the preparation of a Vero cell line stably transformed with an HSV-1 inducible SINrep/LacZ replicon cDNA.

Based on the transient studies described in Example 2, Vero cells were used as the host cell to prepare a stably transformed cell line that could be induced to produce SINrep/LacZ RNA after infection with HSV-1. Subconfluent (50–60%) Vero cells in 35 mm dishes were transfected with pICP8SINrep/LacZ and a plasmid containing the hygromycin B gene under control of the SV40 promoter (pMonHygro) at a molar ratio of 5:1 or 10:1 using 6 µl lipofectamine in Opti-MEM (Life Technologies, Gaithersburg, Md.) according to the manufacturer's recommendations for 5 h at 37° C. at which time the media was changed to complete media. At 72 h post transfection, cells were split 1:10 in selective media containing 500 µg/ml hygromycin B, which was then replaced every 3 days. After 3 weeks individual colonies were isolated and the hygromycin B concentration was reduced to 100 µg/ml. A number of clones were selected that exhibited positive staining for β-galactosidase in most of the cells only after infection with HSV-1. Three clones designated V2-33, V2-34, and V2-35 were chosen for further study and were maintained in hygromycin B (Boehringer Mannheim, Indianapolis, Ind.) at 100 µg/ml in DMEM/10% FBS/pen/strep.

To assay for induction of the replicon, transformed Vero clones were either mock-infected or infected with wild type HSV-1 (MOI=10) in the presence of acyclovir in the wells of a 6 well dish. At 24 h post infection 2 ml lysis buffer was added and 10 ml of the extracts was assayed for β-galactosidase activity as described above. Representative data for V2-33 and two subclones of the original cloned V2-34 population (V2-34-8 and V34-17) are shown in FIG. 2, in which the results shown are the mean of duplicate samples. Cell-free extracts from V2-34 and V2-35 also had activity dependent upon infection of the cells with HSV-1.

To determine if functional replicon was being induced by HSV-1 infection, V2-33, V2-34, and V3-45 cells were plated into the wells of a 24 well dish and subconfluent monolayers (50%) of the cells were transfected with the defective helper cDNA plasmid, p987DHBBNeo. After 72 h, the cells were either mock-infected or infected with HSV-1 at a MOI of 5 in the presence of acyclovir. At thirty h post infection, cell extracts (10 µl) were assayed for β-galactosidase activity as described above and the results are shown in FIG. 3A.

Figure 3B:
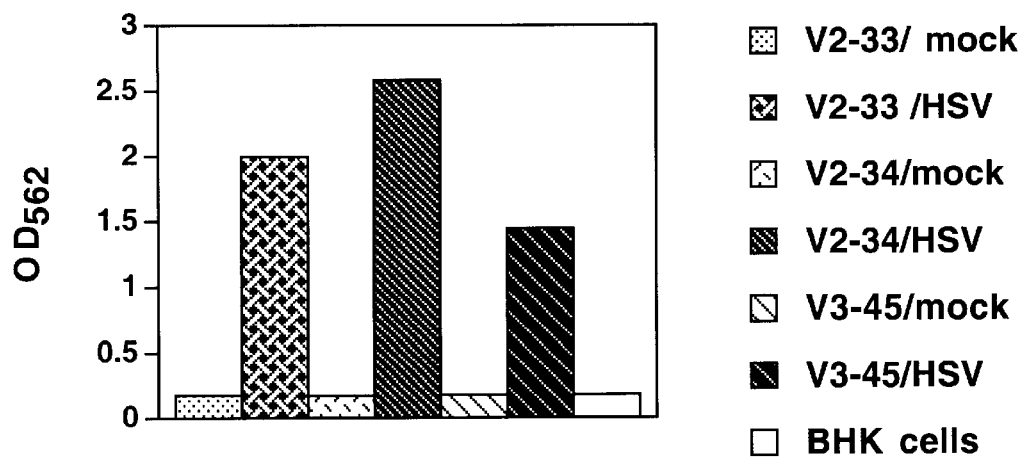

A sample (200 µl) from the media harvested from each of these cultures was inoculated onto BHK cells in the wells of a 24 well dish. Eighteen h later, lysis buffer (250µl) was added to the cells and the extracts assayed for β-galactosidase activity as described above. The results, which are shown in FIG. 3B, indicate that following transfection with a helper plasmid, HSV-1 induced the production of infectious particles that behaved as SINrep/LacZ particles.

Figure 3C:
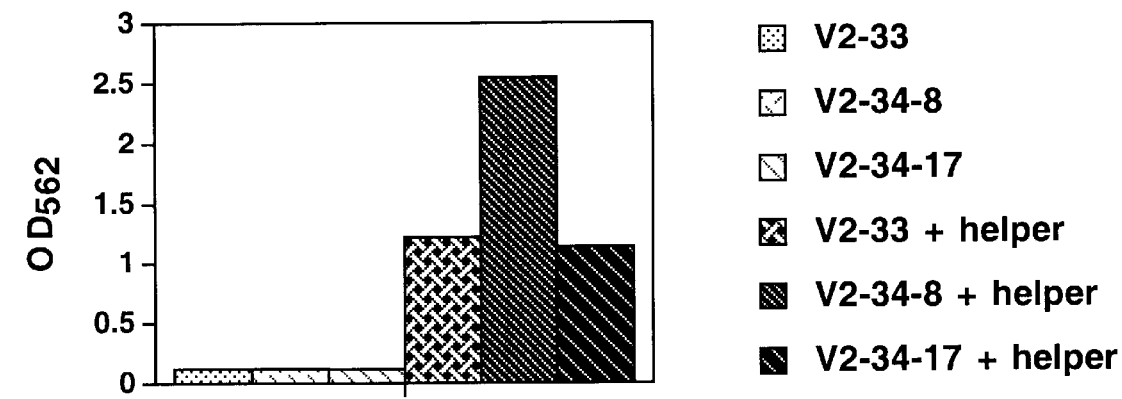

A slightly different protocol was also performed in which the transformed Vero cells were first infected with HSV-1 (MOI=10) and five h post infection the cells were either transfected with the helper plasmid or mock-transfected. The media were collected 18 h later and inoculated onto BHK cells and 18 h later β-galactosidase activity was assayed in cell extracts as described for FIG. 3B. Only samples of the media from HSV-infected cultures which had also been transfected with helper plasmid produced infectious particles, as indicated by the β-galactosidase activity in extracts from BHK cells inoculated with these samples (FIG. 3C). Further support that these cells produced Sindbis replicon particles was provided by the ability of neutralizing antisera to Sindbis virus to substantially inhibit this activity (data not shown, but see FIG. 5).

EXAMPLE 5

This example illustrates the preparation and analysis of a cell line stably transformed with both an HSV-1 inducible replicon cDNA and a helper cDNA.

Based on the above observation that HSV-1 induced production of packaged replicons in transformed Vero cells transfected with a helper plasmid, the inventors herein attempted to isolate stable cell lines that carried both the pICP8SINrep/LacZ cDNA and the defective helper cDNA. V3-45 cells were transfected with p987DHBBNeo using 1 μg DNA plus 6 μl lipofectamine per 35 mm dish for 5 h at 37° C. in Opti-MEM. Seventy-two h post-transfection, the cells were seeded in selective media containing 100 μg/ml hygromycin and 5 mg/ml G418. One week later when no control cells survived, G418 was decreased to 1 mg/ml, and two weeks later to 400 μg/ml. Individual colonies were isolated and expanded in media containing hygromycin B (100 μg/ml) and G418 (400 μg/ml).

Figure 4A:
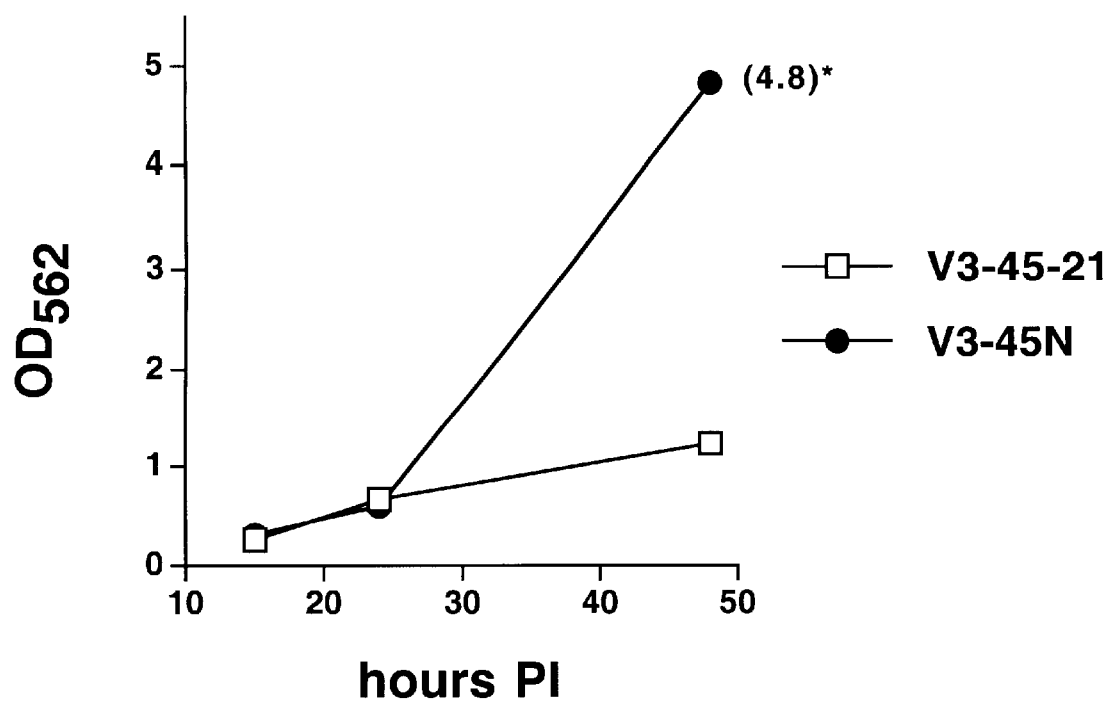
FIGS. 4A–B show a graph of HSV-1 induced β-galactosidase activity in Vero cell lines stably transformed with both pICP8SINrep/lacZ and the defective helper cDNA p987DHBBNeo (V3-45N) or with only pICP8SINrep/lacZ (V3-45-21), with the data point indicated with an asterix (*) obtained by diluting the sample to obtain an $OD_{562}$ reading within the linear range and multiplying the result by the dilution factor.

A cell line, designated V3-45N, was isolated that induced HSV-1-dependent β-galactosidase activity and released infectious particles into the media. Extracts from a subclone (V3-45-21) of the original V3-45 cells and from the V3-45N cells had the same level of β-galactosidase activity at 24 h after infection with HSV-1 (MOI=0.5) in the presence of acyclovir (FIG. 4A). As expected, V3-45-21 cells showed only a small increase from 24 to 48 h. Although the initial MOI of HSV-1 infection was low (0.5), HSV-1 could not spread to uninfected cells because of the presence of acyclovir, and, in the absence of a packaging helper, there would be no spread of the Sindbis virus replicon. V3-45N cells, however, exhibited a substantial increase in β-galactosidase activity between 24 and 48 h post-infection indicating that the lacZ-containing replicon was spreading in these cultures.

Figure 4B:
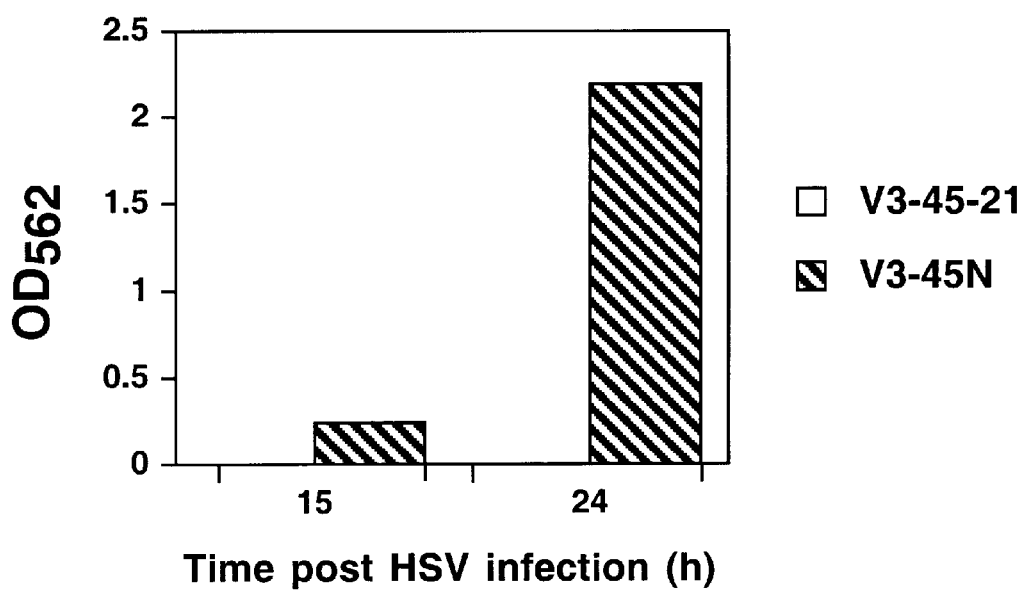

Also, infectious particles were present in the media from HSV-1-infected V3-45N cells, but not from HSV-1 infected V3-45-21 cultures. This was determined by inoculating BHK cells in the wells of a 24 well dish with a sample of the media (50 μl of 2 ml) from the HSV-1-infected cells at 15 and 24 h post infection. Eighteen h later the BHK cells were treated with 200 μl lysis buffer and 10 μl of extract was assayed for β-galactosidase activity. The results are shown in FIG. 4B.

Figure 5:
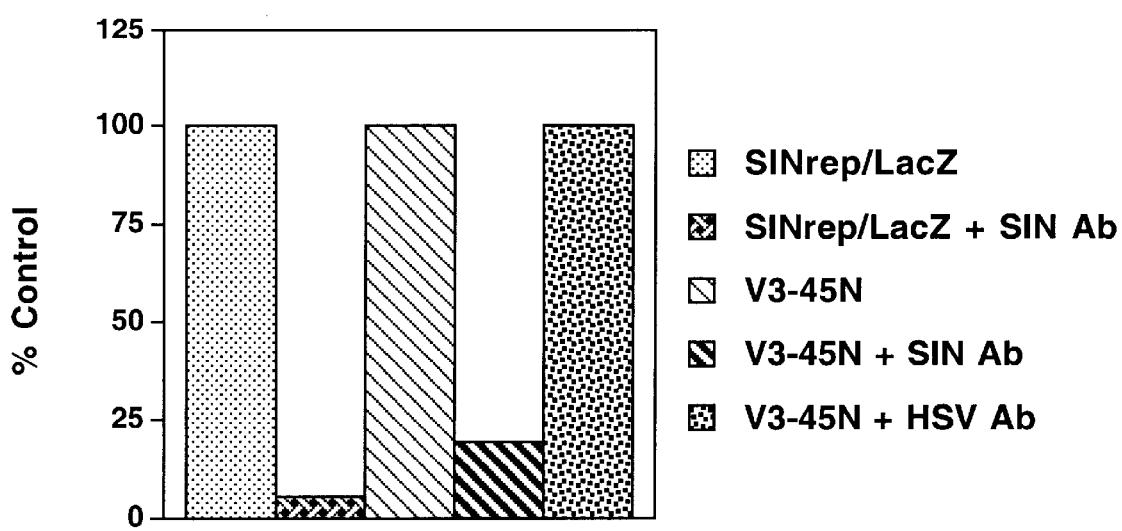
FIG. 5 shows a bar graph comparing β-galactosidase activity in BHK cells inoculated with media from V3-45N cell cultures that were untreated or that were preincubated with neutralizing antisera to Sindbis virus (SIN Ab) or neutralizing antisera to HSV (HSV Ab), with the values obtained from untreated samples designated as 100%.

To verify the identity of the particles released into the media from HSV-1-infected V3-45N cells, a sample (100 μl) from the media was incubated with neutralizing rabbit antisera to Sindbis virus (SIN Ab; 1:250, final dilution) in 500 μl for 1 h at room temperature. A sample of authentic SINrep/LacZ (titer 2×10*/ml) was diluted 1:1000 and was also incubated with the SIN antiserum. After the incubation, a 20 μl sample was used to infect BHK cells in 12 well dishes. Eighteen h later lysis buffer (200 μl) was added and 50 μl of the extract was assayed for β-galactosidase activity as described above. The results are shown in FIG. 5, with the values obtained for samples not treated with antisera designated as 100%. The particles released from the HSV-1-infected V3-45N cells were neutralized by antisera directed against Sindbis virus but not by anti-HSV antiserum, thus verifying that they were Sindbis virus replicons.

The HSV-1 induced spread of SINrep/LacZ in V3-45N cells indicated that these cells might provide a very sensitive means for detecting HSV-1. In preliminary experiments, less than 10 pfu of HSV-1 led to an 8-fold induction of β-galactosidase activity (data not shown).

EXAMPLE 6

This example illustrates the induction of SINrep/LacZ by HSV-1 mutants.

Figure 6A:
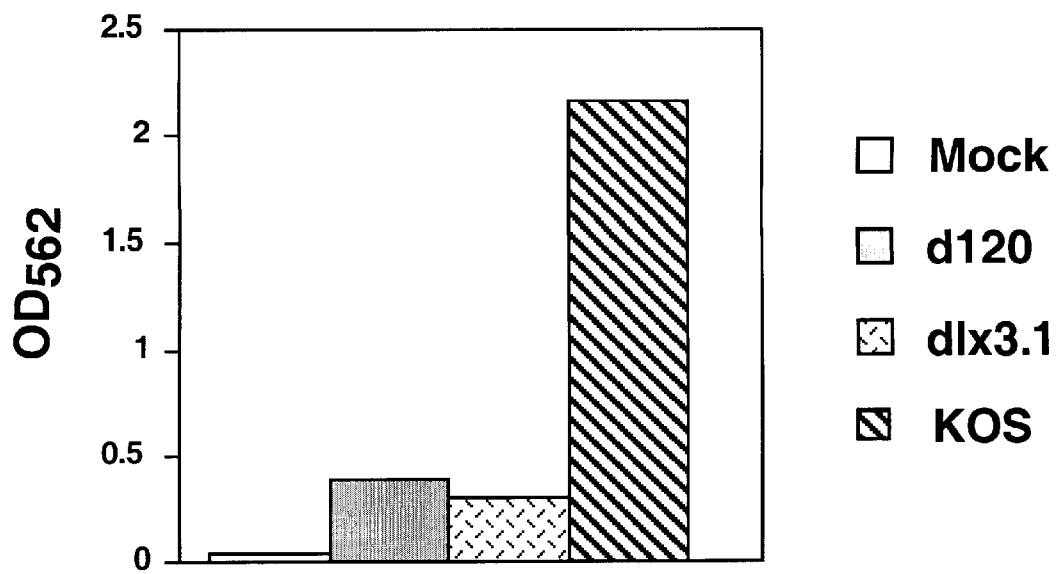
FIGS. 6A–B illustrate induction of the Sindbis replicon in V3-45N cells by HSV-1 mutants defective in one of the major transactivator proteins for ICP8 showing (FIG. 6A) β-galactosidase activity in V3-45N cells mock-infected or infected with wild-type HSV-1 (KOS) or HSV-1 mutants dlx3.1 in the presence of acyclovir or infected with HSV-1 mutant d120 without acyclovir and (FIG. 6B) the titer of SINrep/lacZ virus particles in media from the V3-45N cultures of FIG. 6A, with the titer determined from the standard curve shown in the insert.

The HSV-1-encoded proteins ICP0 and ICP4 are the major transactivators of the ICP8 promoter and they have been shown to have a synergistic effect on expression of ICP8 and other HSV-1 early genes (Cai, W., et al., *J Virol.* 66:2904–15, 1992; Everett, R. D., *EMBO J* 3:3135–3141, 1984; Gelman, I. H., et al., *Proc. Natl. Acad. Sci. USA.* 82:5265–5269, 1985; Su, L,., et al., *J. of Virol.* 61:615–620, 1987). To determine the effect of each of these proteins on the inducibility of SINrep/LacZ, V3-45N cells were infected with wild type HSV-1 (KOS) or with either of two mutant viruses, one containing a deletion in the gene for ICP0 (dlx3.1) and which replicates poorly (Leib, D. A., et al., *J. Virol.* 63:759–768, 1989) and the other a deletion in the gene for ICP4 (d120) and which is replication incompetent (DeLuca, N. A., et al., *J Virol.* 56:558–570, 1985). In each case virus was added at a MOI=5 and infection with wild-type or dlx3. 1 was done in the presence of acyclovir to prevent synthesis of HSV-1 particles. Twenty-four h after infection the media (2 ml) were collected and cell extracts were prepared. A sample of the media (200 μl) was inoculated onto BHK cells in the wells of a 24 well dish. After 18 h cell extracts were prepared with 200 μl lysis buffer and β-galactosidase activity assayed as described above. The results, which are shown in FIG. 6A, demonstrate that both dlx3. 1 and d120 induced β-galactosidase activity in V3-45N cells though to a lesser degree than wild type virus.

The infectious titer of the SINrep/LacZ particles released from V3-45N cells in these experiments was also determined using the X-gal histochemical stain and counting the number of blue cells. In brief, serial dilutions of a stock of SINrep/LacZ were inoculated onto BHK cell monolayers in the wells (4 cm$^2$) of 12-well dishes. Sixteen h later the cells were fixed and histochemically stained for β-galactosidase. The number of blue cells was determined and this was then correlated with OD$_{562}$ reading from the calorimetric assay performed under a standard set of conditions using extracts from cells infected in parallel. A standard curve was generated (shown in the inset of FIG. 6B) which allowed the determination of the infectious particle titer in samples of media without the tedium of having to count cells under the microscope.

Figure 6B:
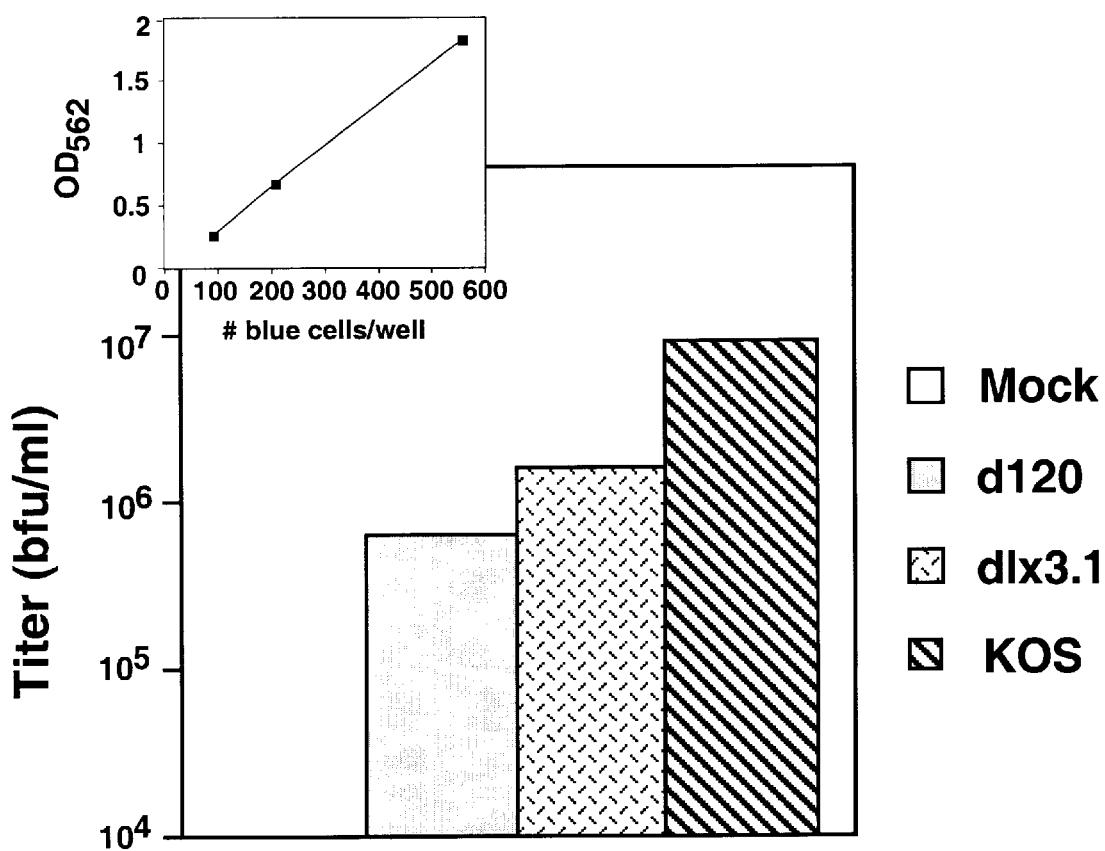

As shown in FIG. 6B, both mutant viruses induced infectious replicon particles, but to a significantly lower level than wild type virus. These results provide evidence that the regulation of SINrep/LacZ in these cells was similar to that of the native ICP8 gene.

A mutant of HSV-1 that contains intact ICP0 and ICP4 genes should activate the ICP8 promoter even if it were unable to replicate. This type of mutant is equivalent to wild type HSV-1 in the presence of acyclovir and would provide another means of activating SINrep/LacZ in the absence of HSV-1 replication. One such replication-defective mutant of HSV-1 is d21, which has a large deletion in the ICP8 gene (Orberg, P. K., et al., *J Virol.* 61:1136–1146, 1987). This mutant was able to induce β-galactosidase in V3-45N cells to essentially the same levels as those obtained with wild type HSV-1 (data not shown).

To examine the distribution of β-galactosidase positive cells in the V3-45N cells and the parental cells (V3-45-21), which were not capable of packaging the replicon, V3-45-21 and V3-45N cells were plated at 80% confluence in the wells (9.5 mm) of a six well dish. The cells were infected with HSV mutant virus d21 (MOI=0.001). Under these conditions, only a small number of cells of the cell monolayer will be infected. Three days after infection the monolayers were fixed and stained for β-galactosidase and the results are shown in FIG. 7.

Figure 7A:
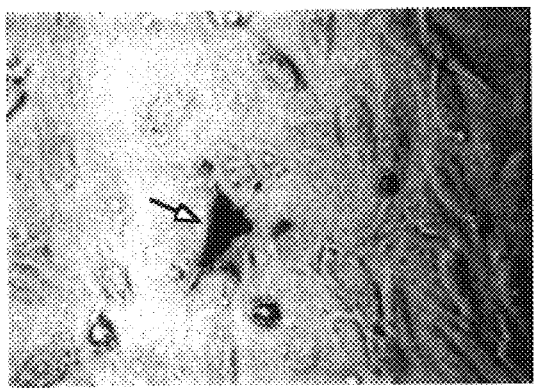
FIGS. 7A–B show photomicrographs of V3-45-21 cells (nonpackaging) (FIG. 7A) and V3-45N cells (packaging) (FIG. 7B) infected with the replication-defective HSV-1 mutant virus d21 and then fixed and histochemically stained for β-galactosidase.
Figure 7B:
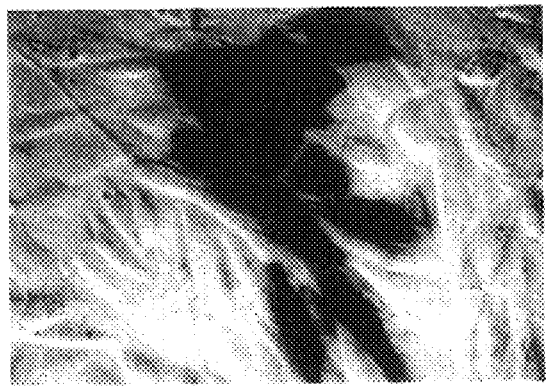

Foci of blue cells were seen in V3-45N cells indicating that SINrep/LacZ particles had spread from a d21-infected cell to neighboring cells (FIG. 7B). In V3-45-21 cells only individual blue cells were observed (FIG. 7A). Most of blue-staining cells looked as though they were dead or dying as would be expected since both d21 and SINrep/LacZ are capable of causing cell death. Many of the blue cells in the V3-45N population retained the appearance of viable cells. They most likely represent cells infected by SINrep/LacZ particles released from previously d21-induced cells and would have been infected for a shorter period of time.

EXAMPLE 7

This example illustrates the preparation of a cell line stably transformed with a human cytomegalovirus-inducible Sindbis replicon.

The model of induction of SINrep/LacZ by herpes virus was tested with HCMV because this virus replicates well only in primary human cells that can not be used to establish stable cell lines (Mocarski, E. S., Jr. 1996. Cytomegaloviruses and Their Replication, p. 2447–2492 in *Virology*, B. Fields (ed.), Lippincott-Raven, New York). HCMV infects mink lung cells, and although it does not complete its replication cycle in these cells, infected cells do express some of the immediate-early and early genes (14). Based on the above results that HSV-1 was able to induce SINrep/LacZ without undergoing a complete replication cycle, mink lung cells were used to prepare stably transformed cell lines analogous to those described above for HSV-1.

First, a plasmid (pUL45SINrep/LacZ) was constructed in which the cDNA of Sinrep/LacZ was placed immediately downstream and under the regulatory control of the HCMV promoter from the UL45 gene, an early gene that encodes a homolog of the HSV-1 ribonucleotide reductase large subunit (Bankier, A. T., et al., *DNA Seq.* 2:1–12, 199 1; Chee, M. S., et al., *Curr Top Microbiol Immunol.* 154:125–169, 1990). To isolate the UL45 promoter, the Hind III M fragment of the HCMV (Towne strain) genome was cloned into pBR322 to generate pCMHM. The UL45 promoter was isolated from pCMHM as a 657 bp Sma I fragment which was cloned into pUC18. Finally the UL45 promoter was cloned as a Xma III to Xho I fragment in front of SINrep/LacZ cDNA. The 5' terminus of the transcript from the UL45 gene has not been mapped so for this construct the start of transcription was estimated using the apparent TATA sequence element.

Preliminary tests with pUL45SINrep/LacZ in transient transfection assays in mink lung cells showed that HCMV-infected cells, but not uninfected cells, produced β-galactosidase (data not shown). Based on these results, mink lung cells were co-transfected with pUL45SINrep/LacZ (2 μg) and pMonHygro (0.1 μg) or with pCMVUL45/LacZ (1 μg) and pMonHygro (0.1 μg). Forty h later the cells were treated with hygromycin B (500 μg/ml) for 7 days. After 3 weeks individual colonies were isolated, expanded in media containing hygromycin B (100 μg/ml) and evaluated for HCMV-inducible β-galactosidase activity.

Figure 8:
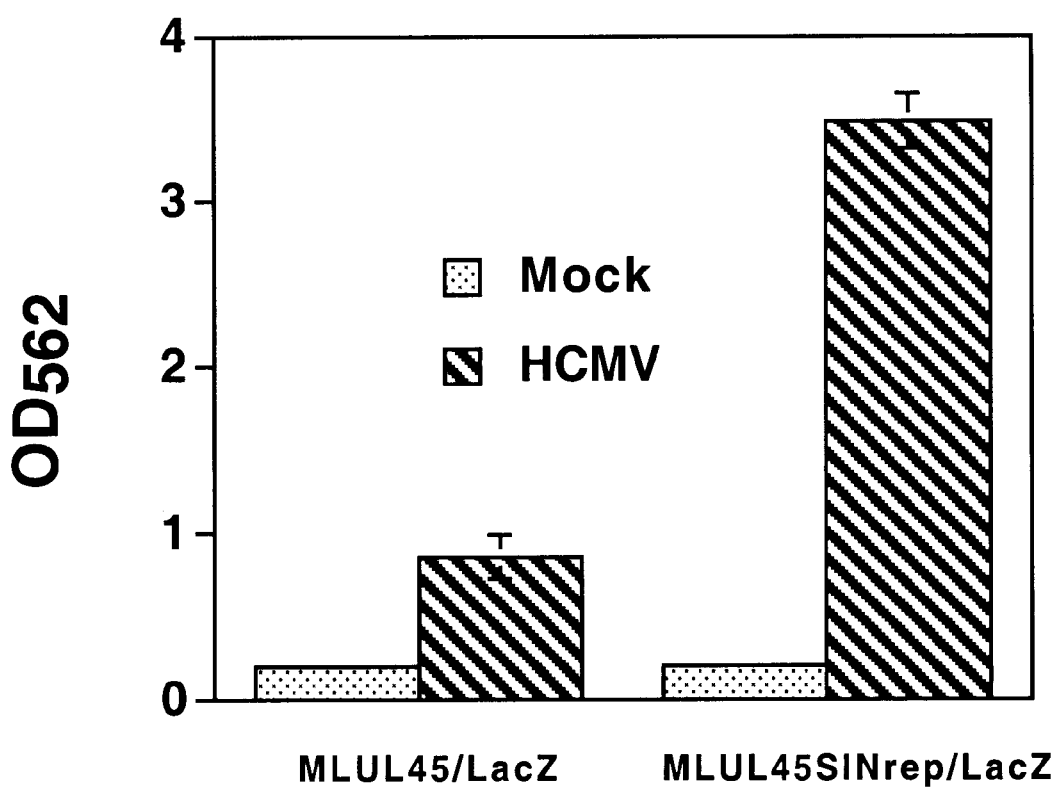
FIG. 8 shows a bar graph of β-galactosidase activity in mink lung cells stably transformed with a chimeric gene containing the lacZ gene under the control of the UL45 beta-gene promoter from human cytomegalovirus HCMV (MLUL45/LacZ) or stably transformed with a cDNA of a SINrep/LacZ replicon under the control of the HCMV UL45 romoter (MLUL45SINrep/LacZ) and mock-infected or infected with HCMV.

Each cell line was plated in the wells of a 24 well dish. The cells were infected with 50 μl HCMV (AD 169 strain, titer 1×10$^6$ infectious focus units/ml) in the presence of 0.1X TurboTreat (Diagnostic Hybrids, Inc., Athens, Ohio). Forty-eight h after infection the cells were treated with 200 μl lysis buffer and 50 μl of extract was assayed for β-galactosidase activity as described above. The mean of triplicate samples are shown in FIG. 8.

The MLUL45SINrep/LacZ cell line showed many positive cells when stained for β-galactosidase activity only after infection with HCMV. The β-galactosidase activity induced in these cells was significantly higher than that observed in the control cell line (MLUL45/LacZ) transformed with a DNA construct in which the lacz gene is directly under the regulatory control of the UL45 promoter.

Unlike the results obtained with HSV-1-infected V3-45 cells transfected with a helper cDNA, no packaged replicons were obtained from HCMV-infected MLUL45SINrep/LacZ cells transfected with the helper plasmid 987DHBBneo. This result was not surprising since Sindbis virus and the SINrep/LacZ replicon replicate poorly in mink lung cells. When mink lung cells were infected with Sindbis virus at a high MOI the yields of virus were more than 100-fold lower than those obtained in BHK cells (data not shown). Other studies have shown that replicons that produce low levels of genomic RNA in BHK cells are packaged much less efficiently than the wild type replicon (Dryga, S., I. Frolov, and S. Schlesinger. unpublished results). In addition, preliminary observations suggest that interferon induction may be contributing to the poor growth of Sindbis virus and this could also affect attempts to package Sindbis replicons directly (Schlesinger, S. unpublished results).

Thus, a different method was used to establish the presence of replicons in the HCMV-induced MLUL45SINrep/LacZ cells. In brief, MLUL45SINrep/LacZ cells (2×10$^7$ cells) were pretreated overnight with TurboTreat reagent (Diagnostic Hybrid, Inc., Athens, Ohio) and were either mock-infected or infected with HCMV (MOI=2) in the presence of a 10-fold dilution of TurboTreat reagent. At forty h post-infection cells were harvested on ice and resuspended in TRIZOL reagent (Life Technologies, Gaithersburg, Md.). Total RNA was isolated following the manufacturer's procedure. Polyadenylated RNA was isolated from this total RNA preparation by chromatography on oligo (dT)-cellulose or by immobilization on streptavidin magnetic particles as recommended by the manufacturer (Boehringer Mannheim, Indianapolis, Ind.). Total RNA (360 μg) and polyA RNA (6–12 pg) were obtained from 2×10$^7$ cells.

The polyA RNA was then co-electroporated into BHK cells with defective helper RNA transcribed in vitro from DHEB (Bredenbeek, P. J., et al., *J. Virol.* 67:6439–6446, 1993). This is essentially the protocol used for packaging of SINrep/LacZ transcripts, but in this case the (putative) replicon RNA came from MLUL45SINrep/LacZ cells. Several different amounts (2, 20, and 200 ng) of SINrep/LacZ RNA, transcribed in vitro were also co-electroporated into BHK cells with DHEB RNA as a positive control. After 24 h, media from the BHK cells were collected and samples taken to infect naive BHK cells. Twenty-four h later the cells were treated with 250 μl lysis buffer and 50 μl of extract was assayed for β-galactosidase activity.

Figure 9:
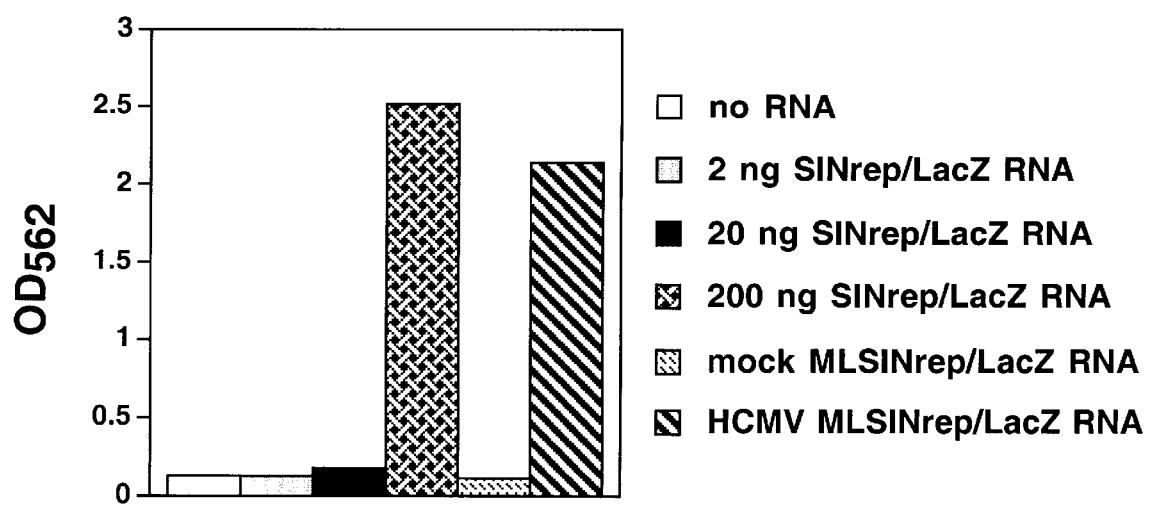
FIG. 9 shows a bar graph of β-galactosidase activity in naive BHK cells infected with media from BHK cells transfected with polyA RNA samples isolated from mock-infected or HCMV-infected MLUL45SINrep/LacZ cells or electroporated with different amounts of SINrep/LacZ replicon RNA.

As shown in FIG. 9, RNA obtained from the MLUI.45SINrep/LacZ cells infected with HCMV contained SINrep/LacZ RNA that was packaged into infectious particles. No packaged particles were detected when the RNA came from uninfected MLUL45SINrep/LacZ cells.

The studies described herein demonstrate that it is possible to obtain stably transformed cell lines in which the Sindbis virus replicon is inducible by herpes viruses. It is believed that such cell lines are useful for any purpose which requires tightly, regulated, high level foreign gene expression. In particular, by providing amplification of the initial virus-induced signal, the cell lines described herein can be used to detect extremely small numbers of infectious DNA virions and/or to detect herpes viruses that replicate poorly in cultured cells.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated by reference. The discussion of references herein is intended merely to summarize the assertions made by their authors and no admission is made that any reference constitutes prior art. Applicants reserve the right to challenge the accuracy and pertinency of the cited references.

4. The recombinant cell according to claim 2, wherein the silent promoter is from the DNA virus.

5. The recombinant cell according to claim 3 wherein the replicon is a packaging competent replicon.

6. The recombinant cell according to claim 3 wherein the replicon is a packaging-defective replicon and the cell further comprises a second polynucleotide comprising a cDNA of a defective helper RNA virus operably linked to a polymerase II promoter or to a promoter inducible by the DNA virus.

What is claimed is:

1. A recombinant cell which is capable of supporting replication of a replicon of a positive-strand RNA virus, wherein the cell is stably transformed with a polynucleotide comprising a silent promoter, inducible by a DNA virus, said silent promoter operably linked to a cDNA of the replicon of the positive-strand RNA virus, wherein the replicon comprises a nucleotide sequence encoding at least one recombinant protein and wherein transcription of the cDNA is dependent upon the presence of the DNA virus.

2. The recombinant cell according to claim 1, wherein the positive-strand RNA virus is a member of a virus family selected from the group consisting of Togaviridae, Astroviridae, Flaviviridae, Picornaviridae and Nodaviridae.

3. The recombinant cell according to claim 1 which packages the replicon into infectious particles of the RNA virus upon infection of the cell by the DNA virus.

7. The recombinant cell according to claim 4, wherein the DNA virus is a herpes virus and the silent promoter is from a beta gene of the herpes virus.

8. The recombinant cell according to claim 4, wherein the recombinant protein is a reporter gene product.

9. The recombinant cell according to claim 8, wherein the reporter gene product is β-galactosidase, chloramphenical acetyl transferase, luciferase, alkaline phosphatase, green fluorescent protein or β-glucuronidase.

10. The recombinant cell according to claim 9, wherein the DNA virus is human cytomegalovirus, the promoter is from the UL45 gene and the positive-strand RNA virus is a Sindbis virus.

11. A method for detecting a DNA virus in a sample comprising the steps of:

(a) incubating the sample with a recombinant cell for a time period sufficient for the infectious cycle of the DNA virus to proceed and for replication of a transcribed replicon to occur, wherein the recombinant cell is capable of supporting replication of a replicon of a positive-strand RNA virus and is stably transformed with a polynucleotide comprising a polynucleotide silent promoter from the DNA virus operably linked to a cDNA of the replicon of the positive-strand RNA virus, wherein the replicon comprises a nucleotide sequence encoding a reporter gene product and wherein transcription of the cDNA is dependent upon the presence of the DNA virus; and (b) detecting expression of the reporter gene product, wherein expression of the reporter gene product indicates the presence of the DNA virus in the sample.

12. The method according to claim 11, wherein the positive-strand RNA virus is a member of a virus family selected from the group consisting of Togaviridae, Astroviridae, Flaviviridae, Picornaviridac and Nodaviridae.

13. The method according to claim 11, wherein the recombinant cell packages the replicon into infectious particles of the RNA virus upon infection of the cell by the DNA virus and wherein expression of the reporter gene product is amplified by infection of surrounding cells by said infectious particles.

14. The method according to claim 12, wherein the DNA virus is a herpes virus and the silent promoter is from a beta gene of the herpes virus.

15. The method according to claim 14, wherein the reporter gene product is β-galactosidase, chloramphenical acetyl transferase, luciferase, alkaline phosphatase, green fluorescent protein or β-glucuronidase.

16. The method according to claim 15, wherein the DNA virus is human cytomegalovirus, the promoter is from the UL45 gene and the positive-strand RNA virus is a Sindbis virus.

17. A kit for detecting a DNA virus in a sample comprising a supply of recombinant cells packaged in a container, wherein the recombinant cells are capable of supporting replication of a replicon of a positive-strand RNA virus and are stably transformed with a polynucleotide comprising a silent promoter from the DNA virus operably linked to a cDNA of the replicon of the positive-strand RNA virus, wherein the replicon comprises a nucleotide sequence encoding a reporter gene product and wherein transcription of the cDNA is dependent upon the presence of the DNA virus.

18. The kit according to claim 17, further comprising a supply of reagents necessary to detect expression of the reporter gene product.

19. A method for producing a recombinant protein which comprises:

(a) providing a recombinant cell which is capable of supporting replication of a replicon of a positive-strand RNA virus and is stably transformed with a polynucleotide comprising a silent promoter inducible by an inducing DNA virus, said silent promoter operably linked to a cDNA of the replicon of the positive-strand RNA virus, wherein the replicon comprises a nucleotide sequence encoding the recombinant protein and wherein transcription of the cDNA is dependent upon the presence of the inducing DNA virus;

(b) incubating the recombinant cell with the inducing DNA virus for a time period sufficient for the infectious cycle of the DNA virus to proceed and for replication of a transcribed replicon and expression of the recombinant protein to occur; and (c) isolating the recombinant protein.

20. The method according to claim 19 wherein the positive-strand RNA virus is a member of a virus family selected from the group consisting of Togaviridae, Astroviridae, Flaviviridae, Picornaviridae and Nodaviridae.

21. The method according to claim 20, wherein the silent promoter is from the inducing DNA virus.

22. The method according to claim 21, wherein the inducing DNA virus is a defective, nonreplicating virus.

23. The method according to claim 21, wherein the recombinant cell packages the replicon into infectious particles of the RNA virus upon infection of the cell by the DNA virus and wherein expression of the recombinant protein is amplified by infection of surrounding cells by said infectious particles.

* * * * *

SEQUENCE LISTING

<160> NUMBER OF SEQ ID NOS: 3

<210> SEQ ID NO 1
<211> LENGTH: 397
<212> TYPE: DNA
<213> ORGANISM: Sindbis virus

<400> SEQUENCE: 1

```
tccggacggc gagctgctgc gcggcgcccc ggccggcggc ccggtttatt cgcgtcggcc      60
cggccggccg ggcttatgga ccgccggcgg ccgacaggag agtgacgtag ccggtgggcg     120
tggccgctat tataaaaaaa gtgagaacgc gaagcgttcg cactttgtcc taataatata     180
tatattatta ggacaaagtg cgaaccgttg cgttctcact ttttttataa tagcggccac     240
gcccaccggc tgatgacgcg cggggcgtgg gaggggctgg ggcggaccgg cacgccccca     300
ggtaaagtgt acatatacca accgcatacc tcgagattga cggcgtagta cacactattg     360
aatcaaacag ccgaccaatt gcactaccat cacaatg                             397
```

<210> SEQ ID NO 2
<211> LENGTH: 30
<212> TYPE: DNA
<213> ORGANISM: Herpes Simplex Virus

<400> SEQUENCE: 2

```
gtttgtctgg cggatccgga cggcgagctg                                      30
```

<210> SEQ ID NO 3
<211> LENGTH: 35
<212> TYPE: DNA
<213> ORGANISM: Herpes Simplex Virus

<400> SEQUENCE: 3

```
ccatggctcg aggtatgcgg ttggtatatg tacac                                35
```